United States Patent [19]

Large et al.

[11] 4,341,549

[45] Jul. 27, 1982

[54] PHOSPHONIUM SALTS OF N-PHOSPHONOMETHYLGLYCINE AND THEIR USE AS HERBICIDES AND PLANT GROWTH REGULANTS

[75] Inventors: George B. Large, Orinda; Lawrence L. Buren, Cupertino, both of Calif.

[73] Assignee: Stauffer Chemical Company, Westport, Conn.

[21] Appl. No.: 295,345

[22] Filed: Aug. 24, 1981

[51] Int. Cl.³ .......................... C07F 9/38; A01N 57/00
[52] U.S. Cl. ..................................... 71/86; 260/502.5
[58] Field of Search ...................... 260/502.5 F; 71/86

[56] References Cited

U.S. PATENT DOCUMENTS 3,230,069  1/1966  Preston ..................................... 71/86
3,364,107  1/1968  Berenson et al. ....................... 71/86
3,556,762  1/1971  Hamm .................................... 71/86
3,847,947 11/1974  Epstein ................................... 71/86
3,929,450 12/1975  Hamm et al. ........................... 71/86
3,977,860  8/1976  Franz ................................ 260/502.5
4,233,056 11/1980  Maier ............................... 260/502.5

Primary Examiner—Joseph E. Evans
Attorney, Agent, or Firm—Harry A. Pacini

[57] ABSTRACT

Novel phosphonium salts of N-phosphonomethylglycine are disclosed herein, having the formula

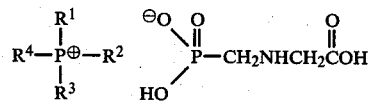

in which $R^1$, $R^2$, $R^3$, and $R^4$ are independently selected from the group consisting of $C_1$–$C_{10}$ alkyl and phenyl. The compounds are useful as herbicides and plant growth regulants.

23 Claims, No Drawings

PHOSPHONIUM SALTS OF N-PHOSPHONOMETHYLGLYCINE AND THEIR USE AS HERBICIDES AND PLANT GROWTH REGULANTS

BACKGROUND OF THE INVENTION

This invention is directed to novel chemical compounds and to their use as herbicides and plant growth regulants. Specifically, this invention relates to phosphonium salts of N-phosphonomethylglycine.

N-Phosphonomethylglycine is a well-known chemical agent, sold commercially as the mono-isopropylamine salt for herbicide applications and as the sodium salt for the growth regulation of sugar cane. The manufacturer is Monsanto Agricultural Products Company, St. Louis, Mo. Various other salts are known, including substituted ammonium salts, alkali metal salts, and alkaline earth metal salts.

A new class of salts of N-phosphonomethylglycine has now been discovered to be effective as postemergence herbicides and plant growth regulants. Whether a herbicidal or growth regulant effect will be achieved depends on the crop to which the salts are applied, the method of application, the type and extent of weeds present, and the application rate. Determination of the proper combination of such factors is well within the routine skill of those skilled in the art of agriculture.

Herbicidal effects range from partial control to complete kill of weeks or generally undesired vegetation. Partial rather than complete control is sometimes preferred for purposes of economics or minimization of accompanying crop injury (depending on the crop to be protected). Plant growth regulant effects are somewhat more varied and include defoliation and retardation of vegetative growth.

Defoliation can be used to enhance the growth of productive plant parts and to facilitate harvesting. This is particularly useful in flax, cotton, and bean crops. Although defoliation kills leaves, it does not harm the rest of the plant and is thus not a herbicidal action. In fact, killing the plant itself is detrimental to defoliation since leaves adhere more strongly to a dead plant.

The retardation of vegetative growth is useful in a variety of ways. In certain plants it causes a diminution or elimination of the normal apical dominance, leading to a shorter main stem and increased lateral branching. Smaller, bushier plants with increased resistance to drought and pest infestation are the result. Retardation of vegetative growth is also useful in turf grasses for lessening the vertical growth rate, enhancing root development, and producing a denser, sturdier turf. The retardation of turf grasses also serves to increase the interval between mowings of lawns, golf courses and similar grassy areas. In silage crops, potatoes, sugar cane, beets, grapes, melons and fruit trees, the retardation of vegetative growth increases the carbohydrate content of the plants at harvest. It is believed that growth retardation or suppression at the appropriate stage of development decreases the amount of carbohydrate available for vegetative growth and thereby enhances starch and/or sucrose content. Retardation of vegetative growth in fruit trees produces shorter branches and greater fullness of shape, and often results in lesser vertical elongation. These factors contribute to the ease of access to the orchard and simplify the fruit harvesting procedure.

BRIEF DESCRIPTION OF THE INVENTION

The present invention resides in a novel class of N-phosphonomethylglycine salts having utility in controlling undesirable vegetation and in regulating the natural growth or development of plants. These salts have the formula

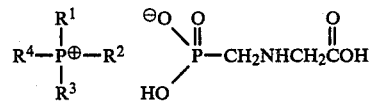

in which $R^1$, $R^2$, $R^3$, and $R^4$ are independently selected from the group consisting of $C_1$–$C_{10}$ alkyl and phenyl.

Within the scope of the above formula, certain embodiments are preferred, namely those in which $R^1$, $R^2$, $R^3$, and $R^4$ are independently selected from the group consisting of $C_1$–$C_6$ alkyl and phenyl. Most preferred are those in which $R^1$, $R^2$, $R^3$, and $R^4$ are identical and are selected from the group consisting of $C_1$–$C_4$ alkyl and phenyl.

This invention further relates to a method of controlling undesirable vegetation, comprising applying to such vegetation in the postemergence state a herbicidally effective amount of a compound having the above formula.

In addition, this invention relates to a method of regulating the natural growth or development of plants, comprising applying to said plants a regulating, non-lethal amount of a compound having the above formula.

The term "herbicidally effective amount" designates any amount of the compounds disclosed herein which will kill a plant or substantially inhibit its growth. By "plants" is meant germinant seeds, emerging seedlings, and established vegetation, including roots and above-ground portions.

The term "natural growth or development" designates the normal life cycle of a plant in accordance with its genetics and environment, in the absence of artificial external influences. A preferred utility of the instant compounds is in increasing the sucrose yield of field grown sugarcane and sorghum. The term "regulating" is used herein to denote the bringing about through chemical means of any temporary or permanent modification or variation from the normal life cycle short of killing the plant.

DETAILED DESCRIPTION OF THE INVENTION

In accordance with the instant invention, weed control is achieved most effectively by applying the compounds to the weeds subsequent to their emergence from the soil. Regulation of the natural growth or development of crops, on the other hand, is achieved by applying the compounds to the crop plants or to any of their above-ground portions at approximately 4 to 10 weeks prior to harvest. For the latter effect, a growth regulating amount is used without herbicidal results. As understood by those skilled in the art, amounts effective for this purpose vary, not only with the particular material selected for treatment, but also with the regulatory effect to be achieved, the species of plant being treated and its stage of development, and whether a permanent or transient regulating effect is sought. Other factors which determine the appropriate amount include the manner of application and weather conditions such as temperature and rainfall. The resulting regulation may arise from the effect of the chemical regulant on either the physiological processes of the plant or the morphology of the plant, or from both in combination or in sequence.

Morphological changes are generally evidenced by changes in the size, shape, color or texture of the treated plant or any of its parts, as well as in the quantity of fruit or flowers the plant produces. Physiological changes, on the other hand, occur within the treated plant and are usually hidden from view. Changes of this type most often occur in the production, location, storage or use of chemicals naturally occurring in the plant, such as hormones. Accompanying changes in morphology may be evidence of such changes, as are various analytical procedures known to those skilled in the art. Regulatory effects occur in a number of diverse ways, varying from one plant species to the next or from one application rate to the next.

The compounds of this invention are readily prepared from N-phosphonomethylglycine by reacting the latter with the appropriately substituted phosphonium halide in the presence of propylene oxide. N-Phosphonomethylglycine itself can be prepared by the phosphonomethylation of glycine, the reaction of ethyl glycinate with formaldehyde and diethylphosphite, or the oxidation of the N-phosphinomethylglycine. Such methods are described in U.S. Pat. No. 3,799,758 (Franz, Mar. 26, 1974).

The examples which follow are intended to be merely illustrative, non-limiting demonstrations of the preparation of the compounds of the instant invention and of their effectiveness in controlling undesirable vegetation and in regulating plant growth.

EXAMPLE 1

Preparation of Mono-tetra-n-butylphosphonium Salt of N-Phosphonomethylglycine

A sample of the mono-isopropylamine salt of N-phosphonomethylglycine was obtained from Monsanto Agricultural Products Co., St. Louis, Mo., in the form of an aqueous solution containing 41% active ingredient by weight. A 51.5 g (0.125 mole) portion of this solution was diluted with 75 ml of water and 10.4 ml of 12 N hydrochloric acid (0.125 mole) was added. The reaction mixture was stirred for an hour, and the solid product was filtered off. The product was washed successively with water, ethanol, and acetone, then dried in an oven. The yield was 15.8 g (75% of theoretical) of N-phosphonomethylglycine.

A 3.4 g (0.02 mole) portion of this material was combined with 6.8 g (0.02 mole) of tetra-n-butylphosphonium bromide and 20 ml of propylene oxide in 100 ml of water. The mixture was warmed gently at 50° C. for thirty minutes, then stripped of water and volatiles to yield 11.0 g of a clear oil with a refractive index of $n_D^{30}=1.5851$. The identity of the product was confirmed as the mono-tetra-n-butylphoshonium salt of N-phosphonomethylglycine by carbon-13 nuclear magnetic resonance and infrared spectroscopy.

EXAMPLE 2

Preparation of Mono-Tetramethylphosphonium Salt of N-Phosphonomethylglycine

A 1.4 g (0.0083 mole) portion of the N-phosphonomethylglycine prepared in Example 1 was combined with 1.8 g (0.0083 mole) of tetramethylphosphonium iodide in 100 ml of water. The mixture was warmed to 50° C. and stirred for one hour. It was then cooled to 15° C. and 6 ml of propylene oxide were added. Stirring was continued at room temperature for an additional two hours. The reaction mixture was then extracted with 150 ml of diethyl ether. The aqueous phase was then stripped to yield 30 g of product which was then dissolved and stripped further with tetrahydrofuran and ether to yield 2.3 g of a solid product showing decomposition at 80° C. The identity was confirmed as the monotetramethylphosphonium salt of N-phosphonomethylglycine by carbon-13 nuclear magnetic resonance.

EXAMPLE 3

Preparation of Mono-tetraphenylphosphonium Salt of N-Phosphonomethylglycine

The procedure of Example 2 was followed, using 1.7 g (0.01 mole) of N-phosphonomethylglycine, 4.66 g (0.01 mole) of tetraphenylphosphonium iodide, and 3 ml of propylene oxide. The yield was 62 g of a liquid product with a refractive index of $n_D^{30}=1.5768$, confirmed by carbon-13 nuclear magnetic resonance to be the monotetraphenylphosphonium salt of N-phosphonomethylglycine.

EXAMPLE 4

Herbicidal Activity

This example demonstrates the postemergence herbicidal activity of the compounds prepared in Examples 1, 2, and 3.

Aluminum planting flats measuring 15.2×22.9×8.9 cm were filled to a depth of 7.6 cm with loamy sand soil, containing 50 parts per million (ppm) each of the commercial fungicide cis-N[(trichloromethyl)-thio]-4-cyclohexene-1,2-dicarboximide (Captan) and 17-17-17 fertilizer (percentages of N-$P_2O_5$-$K_2O$ on a weight basis). Several rows were impressed across the width of each flat and a variety of seeds of both grass and broadleaf weed species were planted, one species per row. The weed species used are listed below:

| Broadleaf weeds: | |
|---|---|
| A. Annual morning glory | *Ipomoea purpurea* |
| B. Cocklebur | *Xanthium sp.* |
| C. Jimsonweed | *Datura stramonium* |
| D. Velvetleaf | *Abutilon theophrasti* |
| E. Mustard | *Brassica sp.* |
| F. Nightshade | *Solanum sp.* |
| G. Pigweed | *Amaranthus sp.* |
| Grasses: | |
| H. Yellow nutsedge | *Cyperus esculentus* |
| I. Downybrome | *Bromus tectorum* |
| J. Foxtail | *Setaria sp.* |
| K. Annual ryegrass | *Lolium multiflorum* |
| L. Watergrass | *Echinochloa crusgalli* |
| M. Rox-orange sorghum | |
| N. Wild oat | *Avena fatua* |

The broad leaf species were seeded first, and the grasses were seeded four days later. Ample seeds of each species were planted to produce 20 to 50 seedlings per row after emergence, depending on the size of each plant.

Ten days after the grasses were seeded, the emerged seedlings of all species were sprayed with aqueous solutions of the test compounds. The solutions were prepared to such dilutions that a spray rate of 80 gallons per acre (750 liters per hectare) gave from 0.25 to 4.0 pounds of test compound per acre (0.28 to 4.48 kilograms per hectare) as desired for each test. Additional flats not treated at all were used as standards for measuring the extent of weed control in the treated flats.

Nineteen days later, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Tables I and II, each representing an independent series of tests.

ratings taken thirteen days later, and for the postemergence test, the flats were sprayed ten days after seeding and rated thirteen days later. The results are shown in Table III, where it is clear that the compounds are effective herbicides only when applied postemergence.

TABLE III
HERBICIDE TEST RESULTS
PRE- AND POSTEMERGENCE AT 4 LB/A

| Test Compound | Application | Broadleaf Weeds | | | | Grasses | | | |
|---|---|---|---|---|---|---|---|---|---|
| | | A | D | E | G | H | J | L | N |
| Mono-tetra-n-butyl phosphonium salt | pre-emergence | 0 | 0 | 0 | 0 | 0 | 0 | 0 | 0 |
| | postemergence | 70 | 80 | 95 | 95 | 75 | 100 | 100 | 75 |
| Mono-tetramethyl-phosphonium salt | pre-emergence | 0 | 0 | 0 | 0 | 0 | 0 | 0 | 0 |
| | postemergence | 85 | 100 | 100 | 100 | 85 | 100 | 100 | 100 |
| Mono-tetraphenyl phosphonium salt | pre-emergence | 0 | 0 | 0 | 0 | 0 | 0 | 0 | 0 |
| | postemergence | 98 | 85 | 100 | 90 | 65 | 100 | 95 | 90 |

EXAMPLE 6

Plant Growth Regulant Activity

This example demonstrates the activity of the mono-tetra-n-butylphosphonium and mono-tetramethylphosphonium salts of N-phosphonomethylglycine in regulat-

TABLE I
HERBICIDE TEST RESULTS

| Test Compound | Application Rate (lb/A) | Percent Control | | | | | | | | | | | | | |
|---|---|---|---|---|---|---|---|---|---|---|---|---|---|---|---|
| | | Broadleaf Weeds | | | | | | | Grasses | | | | | | |
| | | A | B | C | D | E | F | G | AVE | H | I | J | K | L | M | N | AVE |
| Mono-tetra-n-butyl-phosphonium salt | 0.5 | 35 | 40 | 35 | 40 | 50 | 30 | 35 | 38 | 50 | 70 | 100 | 98 | 90 | 85 | 65 | 80 |
| | 1.0 | 50 | 70 | 60 | 60 | 70 | 70 | 45 | 61 | 70 | 75 | 100 | 100 | 95 | 90 | 70 | 86 |
| | 2.0 | 65 | 70 | 70 | 75 | 80 | 75 | 50 | 69 | 75 | 80 | 100 | 100 | 95 | 95 | 75 | 89 |
| | 3.0 | 70 | 75 | 80 | 80 | 90 | 90 | 60 | 78 | 75 | 90 | 100 | 100 | 95 | 98 | 80 | 91 |
| | 4.0 | 75 | 80 | 100 | 95 | 100 | 95 | 85 | 90 | 85 | 100 | 100 | 100 | 98 | 100 | 90 | 96 |

"AVE": average

TABLE II
HERBICIDE TEST RESULTS

| Test Compound | Application Rate (lb/A) | Percent Control | | | | | | | | | | | | | |
|---|---|---|---|---|---|---|---|---|---|---|---|---|---|---|---|
| | | Broadleaf Weeds | | | | | | | Grasses | | | | | | |
| | | A | B | C | D | E | F | G | AVE | H | I | J | K | L | M | N | AVE |
| Mono-tetra-n-butyl-phosphonium salt | 0.25 | 20 | 40 | 40 | 10 | 30 | 30 | — | 28 | 0 | 55 | 100 | 65 | 70 | 25 | 20 | 48 |
| | 0.5 | 60 | 60 | 50 | 30 | 50 | 50 | — | 50 | 40 | 60 | 100 | 75 | 75 | 65 | 60 | 68 |
| | 1.0 | 65 | 65 | 55 | 50 | 70 | 85 | — | 65 | 45 | 70 | 100 | 90 | 100 | 90 | 70 | 81 |
| | 2.0 | 70 | 75 | 60 | 55 | 80 | 95 | — | 73 | 55 | 80 | 100 | 100 | 100 | 100 | 80 | 88 |
| | 3.0 | 75 | 80 | 70 | 70 | 100 | 100 | — | 83 | 65 | 100 | 100 | 100 | 100 | 100 | 90 | 94 |
| Mono-tetramethyl-phosphonium salt | 0.25 | 55 | 50 | 25 | 20 | 60 | 50 | — | 42 | 50 | 70 | 100 | 70 | 85 | 80 | 20 | 68 |
| | 0.5 | 70 | 60 | 40 | 45 | 75 | 80 | — | 62 | 60 | 90 | 100 | 100 | 100 | 100 | 50 | 86 |
| | 1.0 | 80 | 70 | 50 | 75 | 90 | 90 | — | 76 | 70 | 100 | 100 | 100 | 100 | 100 | 90 | 94 |
| | 2.0 | 90 | 80 | 75 | 90 | 95 | 100 | — | 88 | 75 | 100 | 100 | 100 | 100 | 100 | 95 | 96 |
| | 3.0 | 100 | 100 | 100 | 100 | 100 | 100 | — | 100 | 90 | 100 | 100 | 100 | 100 | 100 | 100 | 99 |
| Mono-tetraphenyl-phosphonium salt | 0.25 | 10 | 35 | 10 | 10 | 15 | 50 | — | 22 | 0 | 50 | 90 | 55 | 70 | 60 | 20 | 49 |
| | 0.5 | 35 | 40 | 25 | 20 | 30 | 70 | — | 37 | 10 | 60 | 100 | 70 | 75 | 65 | 45 | 61 |
| | 1.0 | 50 | 50 | 50 | 45 | 75 | 85 | — | 59 | 55 | 75 | 100 | 85 | 90 | 90 | 75 | 81 |
| | 2.0 | 65 | 60 | 70 | 70 | 80 | 90 | — | 73 | 65 | 95 | 100 | 95 | 100 | 100 | 85 | 91 |
| | 3.0 | 75 | 75 | 100 | 80 | 90 | 100 | — | 87 | 75 | 100 | 100 | 100 | 100 | 100 | 95 | 96 |

EXAMPLE 5

Herbicidal Activity

This example demonstrates both the pre-emergence and postemergence activity of the same three compounds on a variety of grasses and broadleaf weeds at an application rate of 4 lb/A (4.48 kilograms per hectare). Many of the same weed species were used (Table III uses the same notations as Tables I and II) and the procedures were similar to those of Example 4, except that for the preemergence test, the flats were sprayed with the test chemicals the day after seeding, and injury ing the growth of sweet sorghum (Sorghum vulgare).

The test procedure was as follows:

A series of fiber pots, 5.0 inches (12.7 cm) in diameter by 5.0 inches (12.7 cm) deep, were filled with sandy loam soil which had been screened and fortified with sufficient 17-17-17 fertilizer to achieve a concentration of 150 ppm each of N, $P_2O_5$, and $K_2O$. A single row of sorghum seeds was planted and the pots were placed in a greenhouse where the temperature was maintained at 27° C. during the day and 21° C. at night. Once the small seedlings emerged, they were thinned to one per pot. Suckers and tillers were removed as they appeared until the plants were treated. The pots were fertilized periodically with 17-17-17 fertilizer.

Nine weeks and four days after seeding, the stalk length to the uppermost visible leaf ligule was measured and the plants were sprayed with a solution of the test compound dissolved in water further containing 0.5% by weight of a polyoxyethylene sorbitan monolaurate surfactant. The spraying system was pressurized by carbon dioxide and mounted on a bicyle-type apparatus. The test solution was sprayed at a rate of 25 gallons per acre (234 liters per hectare), and the concentration of active ingredient was pre-determined to produce application rates ranging from 0.5 to 4.0 pounds of active ingredient per acre (0.56 to 4.48 kilograms per hectare) at this spray rate.

Ten days later, the plants were harvested by cutting the stalks at soil level and removing all leaves and leafsheaths. The length of the stalks to the uppermost visible leaf ligule was again measured. These measurements and those taken on the spraying date were entered into the following formula to determine the "percent stalk elongation":

$$\left.\begin{array}{l}\text{Percent}\\\text{Stalk}\\\text{Elongation}\end{array}\right\} = \left[\frac{\text{length at harvest date}}{\text{length at spray date}} - 1.0\right] \times 100$$

The length of the stalks from the soil level to the uppermost node were then measured and recorded as the "stalk length." The seedhead and peduncle (the portion of the stalk extending from the uppermost node to the base of the seedhead) were then removed and the "fresh weight" of each remaining stalk was recorded. Each stalk was then cut into pieces of about 1.5 inch (3.8 cm) in length and squeezed in a Carver press at 15,000 pounds per square inch (10,340 N/cm$^2$) pressure. The "quantity" of the expressed juice from each stalk was recorded as well as its "total dissolved solids" content in weight percent, as determined by a hand juice refractometer. The crushed stalks were then dried in a forced air oven and weighed ("dry weight").

The results are shown in Table IV, including averaged measurements from three untreated check plants for comparison. The figures indicate a reduction in stalk elongation, fresh weight, and dry weight, and an increase in the percentage of total dissolved solids in the expressed juice, all due to the application of the test compounds.

METHODS OF APPLICATION

For use at a field site, the compounds of the present invention are generally embodied in suitable formulations containing additional ingredients and diluent carriers to aid in their dispersal. Examples of such ingredients or carriers are water, organic solvents, dusts, granules, surface active agents, water-in-oil and oil-in-water emulsions, wetting agents, dispersing agents, and emulsifiers. The formulations generally take the form of dusts, solutions, emulsifiable concentrates, or wettable powders.

A. DUSTS

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bis-naphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Disper-

TABLE IV

| SUGAR ENHANCEMENT TEST RESULTS ON SWEET SORGHUM | | | | | | | |
|---|---|---|---|---|---|---|---|
| | | Percent | Stalk | | | Juice | |
| Test Compound | Application Rate (lb/A) | Stalk Elongation | Length (mm) | F.W. (g) | D.W. (g) | T.D.S. (%) | Quantity (ml) |
| Check* | — | 62.3 | 265 | 42.1 | 3.36 | 4.4 | 9.0 |
| Mono-tetra- | 1.0 | 4.8 | 110 | 10.0 | 1.22 | 7.0 | 1.8 |
| n-butyl | 2.0 | 3.4 | 105 | 10.9 | 1.23 | 7.6 | 3.0 |
| phosphonium salt | 4.0 | 5.3 | 160 | 16.3 | 1.80 | 3.5 | 7.4 |
| Mono-tetra- | 0.5 | 5.4 | 185 | 24.4 | 3.52 | 12.4 | 6.6 |
| methyl- | 1.0 | 2.3 | 255 | 26.2 | 2.75 | 7.0 | 7.6 |
| phosphonium salt | 2.0 | 4.5 | 245 | 23.9 | 2.19 | 7.4 | 8.6 |

"F.W.": fresh weight
"D.W.": dry weight
"T.D.S.": total dissolved solids
*Average of three replications.

sants, when present, constitute up to about 0.5 weight percent, and minor amounts of anticaking and antistatic agents may also be present. The particle size of the entire composition is usually about 30 to 50 microns.

B. SOLUTIONS

Aqueous solutions of the active compounds are prepared such that application at the rate of about 1 to about 200 gallons of solution per acre (about 9 to about 1875 liters per hectare) will provide the required amount of active ingredient. A small amount of nonphytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard.

Suitable anionic surfactants include alkali metal, ammonium, and amine salts of fatty alcohol sulfates having from 8–18 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sorbitan ester. Suitable ampholytic surfactants include secondary and tertiary aliphatic amine derivatives with one aliphatic substituent containing 8 to 18 carbon atoms and another containing an anionic water-solubilizing group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)-propane-1-sulfonate and 3-(N,N-dimethyl-N-hexadecylammonio)-2-hydroxy propane-1-sulfonate.

C. EMULSIFIABLE CONCENTRATES

Emulsifiable concentrates are solutions in which the active materials and an emulsifying agent are dissolved in a non-watermiscible solvent. Prior to use, the concentate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent flocculation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. IN GENERAL

In general, any conventional method of application can be used, including common dusting or spraying equipment. The amount of active ingredient which is effective in producing the desired result, be it herbicidal or growth-regulating, depends on the nature of the plant species to be controlled and the prevailing conditions. Herbicidal effects are usually achieved at 0.1 to 50 pounds active ingredient per acre, preferably 1 to 10, while plant growth regulation is usually achieved at 0.1 to 20 pounds active ingredient per acre, preferably 0.5 to 5. It will be readily apparent to one skilled in the art that compounds of lower activity will require a higher dosage than more active compounds for the same degree of control.

What is claimed is:

1. A compound having the formula

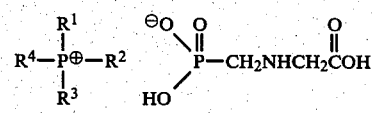

in which $R^1$, $R^2$, $R^3$, and $R^4$ are independently selected from the group consisting of $C_1$–$C_{10}$ alkyl and phenyl.

2. A compound according to claim 1 in which $R^1$, $R^2$, $R^3$, and $R^4$ are independently selected from the group consisting of $C_1$–$C_6$ alkyl and phenyl.

3. A compound according to claim 1 in which $R^1$, $R^2$, $R^3$, and $R^4$ are identical and are selected from the group consisting of $C_1$–$C_4$ alkyl and phenyl.

4. A compound according to claim 1 in which $R^1$, $R^2$, $R^3$, and $R^4$ are each methyl.

5. A compound according to claim 1 in which $R^1$, $R^2$, $R^3$, and $R^4$ are each n-butyl.

6. A compound according to claim 1 in which $R^1$, $R^2$, $R^3$, and $R^4$ are each phenyl.

7. An herbicidal composition comprising an herbicidally effective amount of a compound having the formula

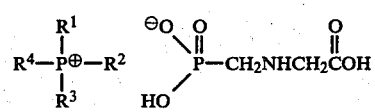

in which $R^1$, $R^2$, $R^3$, and $R^4$ are independently selected from the group consisting of $C_1$–$C_{10}$ alkyl and phenyl and an inert diluent carrier.

8. A composition according to claim 7 in which $R^1$, $R^2$, $R^3$, and $R^4$ are independently selected from the group consisting of $C_1$–$C_6$ alkyl and phenyl.

9. A composition according to claim 7 in which $R^1$, $R^2$, $R^3$, and $R^4$ are identical and are selected from the group consisting of $C_1$–$C_4$ alkyl and phenyl.

10. A composition according to claim 7 in which $R^1$, $R^2$, $R^3$, and $R^4$ are each methyl.

11. A composition according to claim 7 in which $R^1$, $R^2$, $R^3$, and $R^4$ are each n-butyl.

12. A composition according to claim 7 in which $R^1$, $R^2$, $R^3$, and $R^4$ are each phenyl.

13. A method of controlling undesirable vegetation comprising applying to the vegetation in postemergent state an herbicidal composition comprising an herbicidally effective amount of a compound having the formula

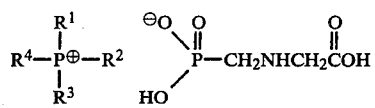

in which $R^1$, $R^2$, $R^3$, and $R^4$ are independently selected from the group consisting of $C_1$–$C_{10}$ alkyl and phenyl, and an inert diluent carrier.

14. A method according to claim 13 in which $R^1$, $R^2$, $R^3$, and $R^4$ are independently selected from the group consisting of $C_1$–$C_6$ alkyl and phenyl.

15. A method according to claim 13 in which $R^1$, $R^2$, $R^3$, and $R^4$ are identical and are selected from the group consisting of $C_1$–$C_4$ alkyl and phenyl.

16. A method according to claim 13 in which $R^1$, $R^2$, $R^3$, and $R^4$ are each methyl.

17. A method according to claim 13 in which $R^1$, $R^2$, $R^3$, and $R^4$ are each n-butyl.

18. A method according to claim 13 in which $R^1$, $R^2$, $R^3$, and $R^4$ are each phenyl.

19. A method of regulating the natural growth or development of plants which comprises applying to said plants a regulating, nonlethal amount of a compound having the formula

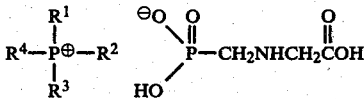

in which $R^1$, $R^2$, $R^3$, and $R^4$ are independently selected from the group consisting of $C_1$–$C_{10}$ alkyl and phenyl, and an inert diluent carrier.

20. A method according to claim 19 in which $R^1$, $R^2$, $R^3$, and $R^4$ are independently $C_1$–$C_{10}$ alkyl.

21. A method according to claim 19 in which $R^1$, $R^2$, $R^3$, and $R^4$ are identical and are each $C_1$–$C_4$ alkyl.

22. A method according to claim 19 in which $R^1$, $R^2$, $R^3$, and $R^4$ are each methyl.

23. A method according to claim 19 in which $R^1$, $R^2$, $R^3$, and $R^4$ are each n-butyl.

* * * * *